United States Patent
Syed et al.

(10) Patent No.: US 11,938,186 B2
(45) Date of Patent: Mar. 26, 2024

(54) THERMOSENSITIVE HYDROGEL FOR CANCER THERAPEUTICS AND METHODS OF PREPARATION THEREOF

(71) Applicant: INDIAN INSTITUTE OF TECHNOLOGY HYDERABAD, Telangana (IN)

(72) Inventors: Baseeruddin Alvi Syed, Sangareddy (IN); Rajalakshmi P. S., Sangareddy (IN); Aravind Kumar Rengan, Sangareddy (IN)

(73) Assignee: Indian Institute of Technology Hyderabad, Telangana (IN)

( * ) Notice: Subject to any disclaimer, the term of this patent is extended or adjusted under 35 U.S.C. 154(b) by 258 days.

(21) Appl. No.: 17/325,290

(22) Filed: May 20, 2021

(65) Prior Publication Data
US 2021/0393780 A1  Dec. 23, 2021

(30) Foreign Application Priority Data
May 20, 2020  (IN) .............................. 202041021283

(51) Int. Cl.
| | |
|---|---|
| *A61K 47/32* | (2006.01) |
| *A61K 9/06* | (2006.01) |
| *A61K 9/127* | (2006.01) |
| *A61K 31/704* | (2006.01) |
| *A61K 33/242* | (2019.01) |
| *A61K 41/00* | (2020.01) |
| *A61K 47/34* | (2017.01) |
| *A61K 47/42* | (2017.01) |
| *A61P 35/00* | (2006.01) |

(52) U.S. Cl.
CPC ............ *A61K 41/0028* (2013.01); *A61K 9/06* (2013.01); *A61K 9/1271* (2013.01); *A61K 31/704* (2013.01); *A61K 33/242* (2019.01); *A61K 47/32* (2013.01); *A61K 47/34* (2013.01); *A61K 47/42* (2013.01); *A61P 35/00* (2018.01)

(58) Field of Classification Search
None
See application file for complete search history.

(56) References Cited

PUBLICATIONS

Giuliano et al (Drug-Loaded Biocompatible Nanocarriers Embedded in Poloxamer 407 Hydrogels as Therapeutic Formulations. Medicines 2019, 6, 7, p. 1-20) (Year: 2019).*
Giuliano et al (Mucosal Applications of Poloxamer 407-Based Hydrogels: An Overview. Pharmaceutics 2018, 10, 159, p. 1-26; herein after "Giuliano2"), (Year: 2018).*
Bercea et al.(Temperature Responsive Gels Based on Pluronic F127 and Poly(vinyl alcohol). Ind. Eng. Chem. Res. 2011, 50, 4199-4206 (Year: 2011).*
And Kamlungmak et al (Lamellar phase behavior and molecular interaction of a thermoresponsive poloxamer and crosslinked poly (vinyl alcohol) hydrogel. Materials Today Communications, https://doi.org/10.1016/j.mtcomm.2019.100542, p. 1-13). (Year: 2019).*
Dreaden et al (The golden age: gold nanoparticles for biomedicine. Chem Soc Rev. Apr. 7, 2012; 41(7): 2740-2779, (Year: 2012 ).*
Liu et al (Codelivery of Doxorubicin and Paclitaxel by Cross-Linked Multilamellar Liposome Enables Synergistic Antitumor Activity. Mol. Pharmaceutics 2014, 11, 1651-1661). (Year: 2014).*

* cited by examiner

*Primary Examiner* — Jake M Vu
(74) *Attorney, Agent, or Firm* — Kolisch Hartwell, P.C.

(57) ABSTRACT

The present invention provides for thermosensitive hydrogel for cancer therapeutic and methods of preparation thereof. The invention represents an advancement in the field of cancer therapeutics and provides for a polymer-protein based thermosensitive hydrogel comprising polyvinyl alcohol, poloxamer 407 and bovine serum albumin. The thermosensitive hydrogel can be optionally be enriched with one or more additional component such as photothermal agents, photosensitizers, drugs and dyes. The invention also provides for a method of preparing the thermosensitive hydrogels. The hydrogels of the present invention are inexpensive, thermosensitive, has ability to effectuate sustained release of drugs and can be used for targeted delivery and dual-modality treatment.

20 Claims, 12 Drawing Sheets

THERMOSENSITIVE HYDROGEL FOR CANCER THERAPEUTICS AND METHODS OF PREPARATION THEREOF

CROSS REFERENCE TO RELATED APPLICATIONS

The present application claims priority from Indian Patent Application No. 202041021283 filed on May 20, 2020, the contents of which are hereby incorporated by reference herein in their entirety.

FIELD OF INVENTION

The present invention pertains to the field of cancer therapeutics. More particularly, the invention relates to a thermosensitive polymer-protein based injectable hydrogel that can form a localized depot within a superficial tumor.

BACKGROUND OF THE INVENTION

Cancer refers to a large group of diseases characterized by the growth of abnormal cells which disregards the normal rules of cell division. Cancer is a leading cause of the fatality which is characterized by the ability of the abnormal cells to metastasize across the body, spreading tumors at multiple sites, consequently leading to the death.

Conventional treatment modalities of cancers include surgery, chemotherapy, radiation therapy, immunotherapy etc. These treatment modalities are inefficient and have major drawbacks due to the complexity and heterogeneity of the tumor microenvironment. Although surgery and/or chemotherapy has significantly improved the outcome and chances of survival, there remains an unmet need in the art to develop more effective therapeutic modalities that can be used for the treatment and management of cancer.

Photo therapies like photothermal therapy (PTT), photodynamic therapy (PDT) and cryotherapy etc. are emerging treatment modalities for the radical cancer treatment owing to its non-invasiveness and high selectivity.

However, treatments like photothermal therapy (PTT), photodynamic therapy (PDT) or chemotherapy are single-modality treatments which are often ineffective for management of cancer due to the usage of single active ingredient. In order to come up with newer and more effective therapeutic strategies for management of cancer, the inventors have envisaged a multidimensional approach of development of dual-modality treatment, which has the potential to combine multiple therapeutic approaches such as combining PTT with chemotherapy (chemo-photothermal therapy), photodynamic therapy (photothermal-photodynamic therapy). Combining the therapeutic approaches can provide synergistic therapeutic efficacy compared to individual treatments.

The inventors have developed a new approach by preparing thermosensitive hydrogels which can be used for combining therapeutic modalities for treatment and management of cancer.

Thus, the present invention is an advancement in cancer therapeutics and management to solve a long-standing problem of providing a highly efficacious therapeutic modality for prevention or treatment of cancer. The invention would enable treatment of cancer more accessible and affordable to a huge population affected by cancer.

SUMMARY OF THE INVENTION

The present invention provides for an injectable thermosensitive hydrogel comprising polyvinyl alcohol, poloxamer 407 and bovine serum albumin. The thermosensitive hydrogel can be optionally be enriched with one or more additional component such as photothermal agents, photosensitizers, vaccines, drugs and dyes. The invention also provides for a method of preparing the thermosensitive hydrogels. The hydrogels of the present invention are inexpensive, thermosensitive, has ability to effectuate sustained release of drugs and can be used for targeted delivery and dual-modality treatment.

DEFINITIONS

Figure 1:
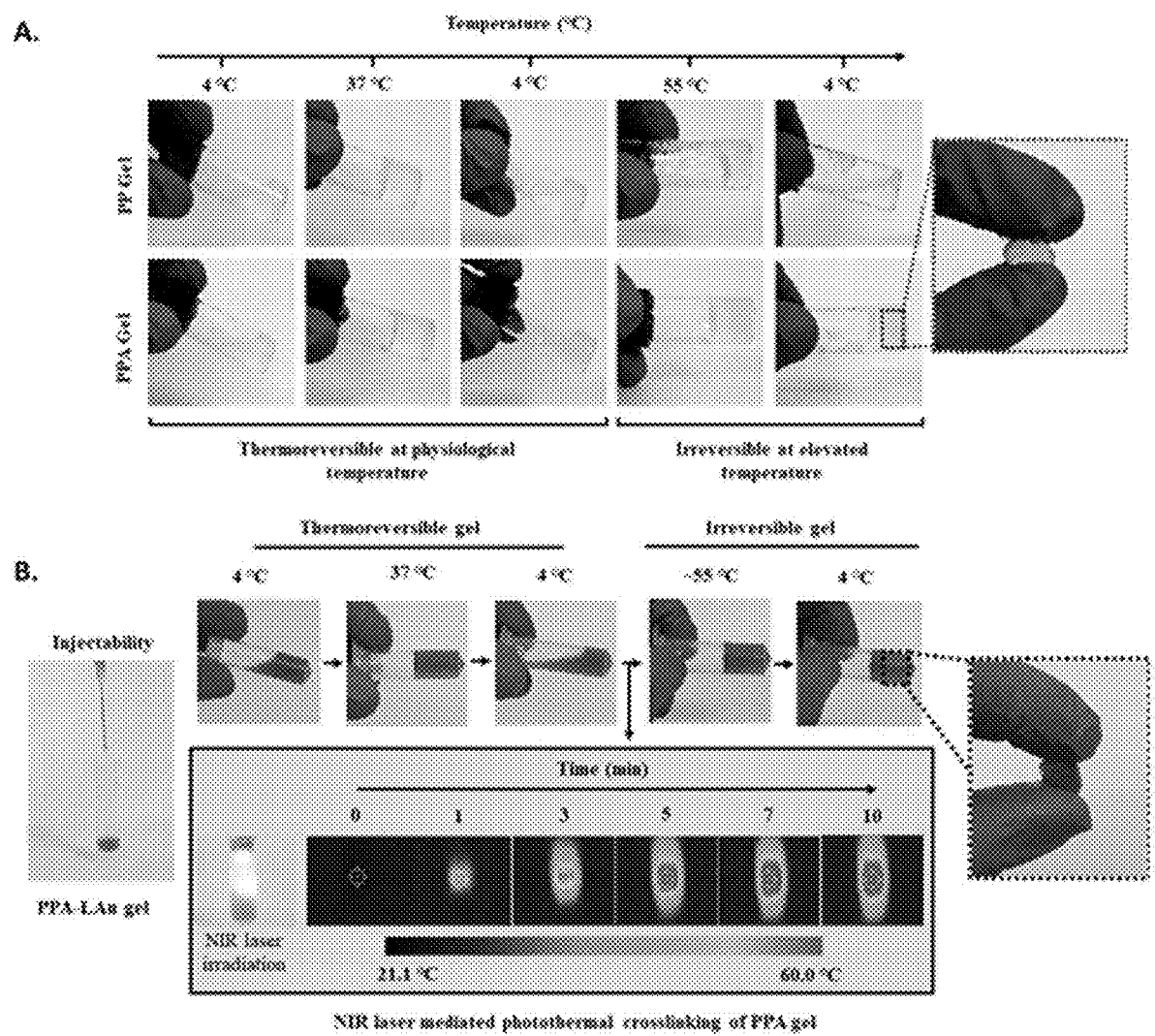
FIG. 1 depicts (A) the thermoreversible/irreversible nature of PPA Gel; (B) Injectability and NIR mediated crosslinking of PPA Gel entrapping LAu NPs.

Embodiments described herein can be understood more readily by reference to the following detailed description, examples, and drawings. Elements, apparatus and methods described herein are merely illustrative of the principles of the present invention and are not limited to the specific embodiments presented in the detailed description, examples, and drawings. Numerous modifications and adaptations will be readily apparent to those of skill in the art without departing from the spirit and scope of the invention.

Unless defined otherwise, all technical and scientific terms used herein have the same meaning as commonly understood by one of ordinary skill in the art to which the methods belong. Although any nanogels, compositions or methods similar or equivalent to those described herein can also be used in the practice or testing of the embodiments of the present invention, representative illustrative methods and compositions are now described.

Where a range of values is provided, it is understood that each intervening value between the upper and lower limit of that range and any other stated or intervening value in that stated range, is encompassed within by the methods and compositions. The upper and lower limits of these smaller ranges may independently be included in the smaller ranges and are also encompassed within by the methods and compositions, subject to any specifically excluded limit in the stated range. Where the stated range includes one or both of the limits, ranges excluding either or both of those included limits are also included in the methods and compositions.

It is appreciated that certain features of the methods, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other embodiments without departing from the scope or spirit of the present methods. Any recited method can be carried out in the order of events recited or in any other order that is logically possible.

The term "drug" as used herein refers to any pharmaceutically effective compound used in the treatment of diseases, such as, but not limited to cancer. Preferably, the drug is hydrophobic in nature.

The phrase "pharmaceutically acceptable carrier" or "pharmaceutically acceptable excipient" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "photothermal therapy" refers to irradiation of laser light within NIR range (650 to 1100 nm) on light absorbing material that converts light energy into heat energy causing hyperthermia. The materials responsive to this therapy could be NIR dyes or metallic nanoparticle. Photothermal therapy in the context of the present invention is effectuated with the use of one or more "photothermal agent".

The term "photodynamic therapy" refers to irradiation of light within NIR range on light absorbing material that produces reactive oxidative species.

The term "chemotherapy" refers to the use of chemotherapeutic drugs (chemicals) for destroying the cancer cells. The term "chemo-photothermal therapy" refers to a combination of both chemotherapy and photothermal therapy.

The term "liposomal nanoparticles" refers to a formulation of liposomes, wherein liposomes are artificially prepared vesicles made of lipid bilayer, which is defined as a thin membrane made of two layers of lipid molecules. Lipid bilayer may be in a form of a single or one lipid bilayer, or of multiple lipid bilayers. Liposomes may be filled or loaded with drugs or active pharmaceutical ingredients. In the context of the present invention, "liposomal nanoparticles" refers to gold-coated nanoparticles prepared by a method described herein.

The term "thermosensitive" as used herein refers to the property of the hydrogels to exhibit a phase a reversible transition from sol to gel at physiological temperature (37° C.) and irreversible transition at elevated temperature (55° C.).

In reference to the treatment or prevention of cancer, an "effective amount" refers to that amount which has the effect of reducing or inhibiting (that is, slowing to some extent, preferably stopping) one or more signs or symptoms characterizing one or more cancer.

DETAILED DESCRIPTION OF THE INVENTION

As those in the art will appreciate, the following detailed description describes certain preferred embodiments of the invention in detail and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only and is not intended to limit the scope of the invention defined by the appended claims.

The present invention discloses thermosensitive hydrogels comprising Polyvinyl Alcohol (PVA), poloxamer 407 (Pluronic-127), Bovine Albumin which can be loaded with one or more photosensitizer, photothermal agent or drug. Further, the invention contemplates a multidimensional approach in development of highly efficacious and cost-effective hydrogels which have synergistic therapeutic effect on cancer cells.

The present invention is characterized by the following advantages:

(a) Affordable: The hydrogels developed are considerably inexpensive and has the potential to act as a cancer therapeutic.

(b) Thermosensitive: The hydrogels when injected in the tumor can exhibit a phase a reversible transition from sol to gel at physiological temperature (37° C.) and irreversible transition at elevated temperature (55° C.) thus forming a depot (Example 3).

(c) Sustained Release: These hydrogels have the potential to be used as a depot for sustained release of nanoparticle for photothermal therapy and/or for micellar delivery of drug/dyes for therapeutics and bio imaging (Example 4).

(d) Dual modality treatment: The hydrogels are extremely effective for dual modality treatment, such as combining photothermal therapy with chemotherapy (chemo-photothermal therapy) or photodynamic therapy (photothermal-photodynamic therapy).

(e) Targeted delivery: The hydrogels can be used for targeted drug delivery to primary & metastasized secondary tumors and for bio-imaging (Example 10).

(f) Absence of undesirable effects: The hydrogels are highly efficacious in treatment of cancer without having any visible side effects (Example 8 and Example 9).

(g) Therapeutic efficacy: The hydrogels combined with model drugs have exhibit higher therapeutic efficacy when compared to drug individually. This is exhibited by Example 8 and Example 9. Further, Example 12 exhibits the inhibition of metastatic tumor.

Figure 4:
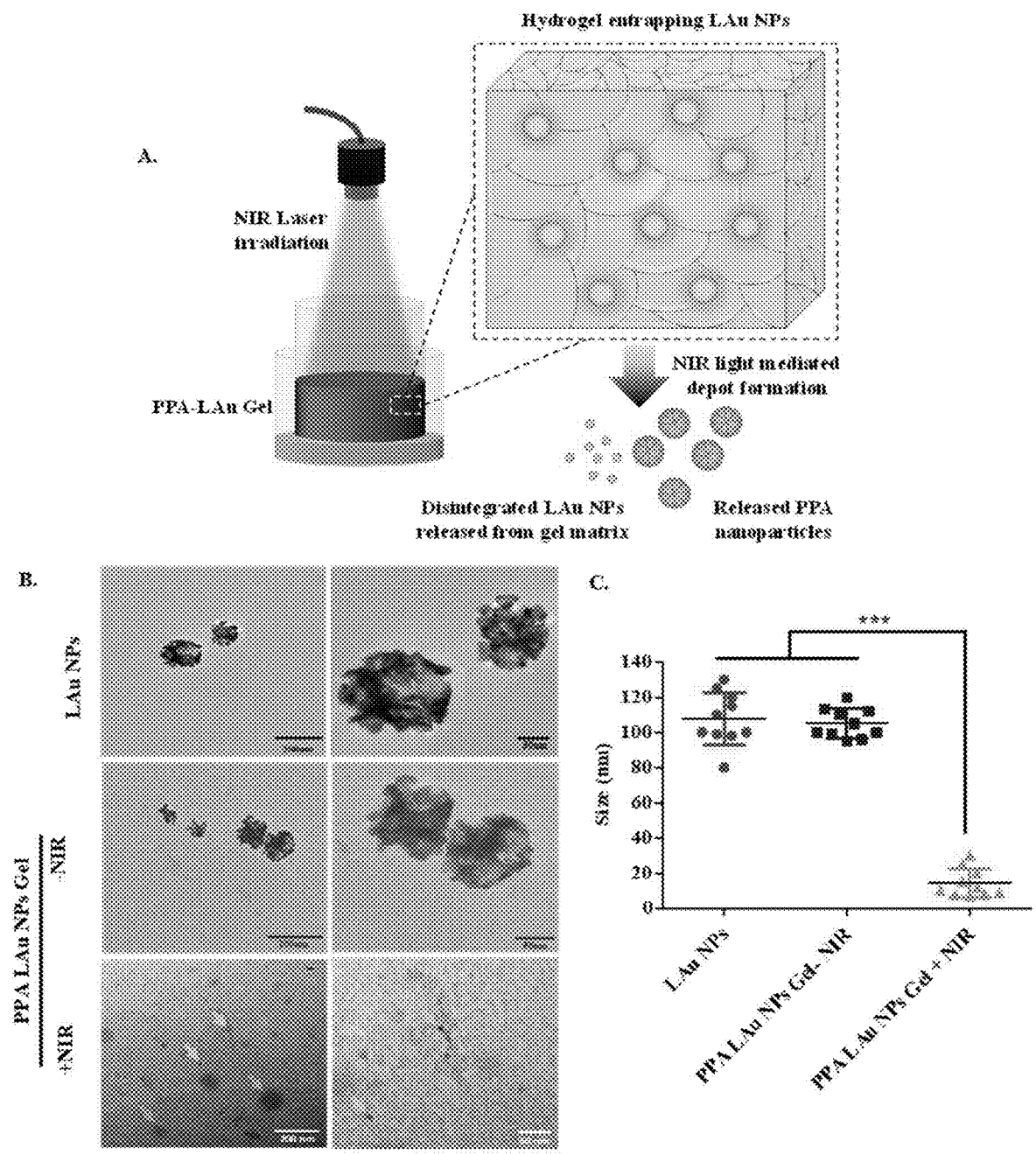
FIG. 4 depicts (A) Schematic representing NIR mediated LAu NPs disintegration in hydrogel matrix on repeated laser irradiation, (B) TEM imaging of LAu NPs extracted from gel (+/−NIR), (C) Quantification of NIR mediated LAu NPs disintegration in hydrogel.

(h) In-situ formation of nanoparticles: It was found that thermosensitive hydrogels loaded with drugs forms in situ nanoparticles and can be used for targeted therapeutics. (Example 7; FIG. 4B and FIG. 4C; Example 11)

Before the hydrogels and methods of the present disclosure are described in greater detail, it is to be understood that the invention is not limited to particular embodiments and may vary. It is also to be understood that the terminology used herein is for the purpose of describing particular embodiments only, and is not intended to be limiting, since the scope of the formulations and processes will be limited only by the appended claims.

In one embodiment, the invention provides a thermosensitive hydrogel comprising one or more polymer and protein.

In one embodiment, the polymer is selected from a group comprising polyvinyl alcohol and poloxamer 407, and combination thereof.

Polyvinyl alcohol is a water-soluble polymer represented by the general formula:

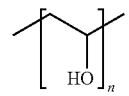

Poloxamer 407 (tradename: Pluronic-F127) is a triblock copolymer consisting of a central hydrophobic block of polypropylene glycol flanked by two hydrophilic blocks of polyethylene glycol (PEG). It is represented by the general formula:

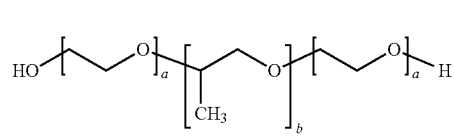

In another embodiment, the hydrogel comprises one or more protein in addition to polymers.

In another embodiment, the protein is bovine serum albumin.

In one embodiment, the concentration of polyvinyl alcohol in the hydrogel is in a range from 2-5% v/v.

In one embodiment, the concentration of poloxamer 407 in the hydrogel is in a range from 22-25% wt/v.

In one embodiment, the concentration of bovine serum albumin in the hydrogel is in a range from 2-8% wt/v.

The protein-polymer based hydrogel of the present invention is characterized by thermosensitivity and ability to delivery one or more active component in a safe and efficacious manner.

In another embodiment, the hydrogel contains one or more additional component selected from a group comprising photothermal agents, photosensitizers, drugs and dyes.

In one embodiment, the photothermal agent in the hydrogel may be selected from a group comprising gold-coated liposomal nanoparticles, photothermal dyes and the like.

In one embodiment, the photothermal agent in the hydrogel is gold-coated liposomal nanoparticles.

In another embodiment, the gold-coated liposomal nanoparticles are present in the hydrogel at a concentration in the range from 1-3 mg/ml.

In another embodiment, the drug in the hydrogel is a hydrophobic drug.

In another embodiment, the drug in the hydrogel is doxorubicin.

In another embodiment, the doxorubicin is present in the hydrogel at a concentration in the range from 50-500 μg/ml.

In another embodiment, the invention provides a thermosensitive hydrogel comprising polyvinyl alcohol and poloxamer 407, wherein the concentration of polyvinyl alcohol in the hydrogel is in a range from 2-6% v/v, the concentration of poloxamer 407 in the hydrogel is in a range from 22-25% wt/v.

In another embodiment, the invention provides a thermosensitive hydrogel comprising polyvinyl alcohol, poloxamer 407 and bovine serum albumin, wherein the concentration of polyvinyl alcohol in the hydrogel is in a range from 2-6% v/v, the concentration of poloxamer 407 in the hydrogel is in a range from 22-25% wt/v and the concentration of bovine serum albumin in the hydrogel is in a range from 2-8% wt/v.

In another embodiment, the invention provides a thermosensitive hydrogel comprising polyvinyl alcohol, poloxamer 407, bovine serum albumin, gold-coated liposomal nanoparticles and doxorubicin, wherein the concentration of polyvinyl alcohol in the hydrogel is in a range from 2-5% v/v, the concentration of poloxamer 407 in the hydrogel is in a range from 22-25% wt/v, the concentration of bovine serum albumin in the hydrogel is in a range from 2-8% wt/v, the concentration of liposomal nanoparticles in the hydrogel is in a range from 1-3 mg/ml and the concentration of doxorubicin in the hydrogel is in a range from 50-500 µg/ml.

In yet another embodiment, the invention provides a method for preparing a thermosensitive hydrogel, comprising:
a. adding polyvinyl alcohol to a solution of poloxamer 407 under constant stirring at a temperature in the range from 2-6° C., wherein the concentration of polyvinyl alcohol is in a range of 2-5% v/v and the concentration of poloxamer 407 is in a range of 22-25% wt/v; and
b. adding 2-8% solution of ice cold bovine serum albumin to the reaction mixture obtained in step (a) under vigorous stirring for about 6 hrs to obtain a thermosensitive hydrogel.

In another embodiment, the thermosensitive hydrogel is optionally enriched with one or more additional component selected from a group comprising photothermal agents (gold based NPs, Copper based NPs, polydopamine etc), photosensitizers (IR 780 dye, IR 820 dye, Photofrin etc) vaccines, proteins and peptides (Insulin, Annexin etc), drugs (curcumin, paclitaxel, palbociclib etc.) and dyes (Nile red, IR806, FITC).

In one embodiment, the model photothermal agent used for enriching the hydrogel is gold-coated liposomal nanoparticles.

In another embodiment, the gold-coated liposomal nanoparticles are added to the hydrogel at a concentration in the range from 1-3 mg/ml.

In another embodiment, the drug used for enriching the hydrogel is a hydrophobic drug.

In another embodiment, the model drug used for enriching the hydrogel is doxorubicin.

In another embodiment, the doxorubicin is added to the hydrogel at a concentration in the range from 50-500 µg/ml.

In yet another embodiment, the invention provides a method for preparing a thermosensitive hydrogel containing gold-coated liposomal nanoparticles and doxorubicin, comprising:
a. adding polyvinyl alcohol to a solution of poloxamer 407 under constant stirring at a temperature in the range from 2–6° C., wherein the concentration of polyvinyl alcohol is in a range of 2-5% v/v and the concentration of poloxamer 407 is in a range of 22-25% wt/v;
b. adding 2-8% solution of ice cold bovine serum albumin to the reaction mixture obtained in step (a) under vigorous stirring for about 6 hrs to obtain a thermosensitive hydrogel;
c. adding gold coated liposomal nanoparticles to the hydrogel obtained in step (b) at a temperature about 4° C. under constant stirring for 10 minutes, wherein the concentration of gold-coated nanoparticles ranges from 1-3 mg/mL to obtain hydrogel containing gold-coated liposomal nanoparticles; and
d. adding doxorubicin to the gold-coated liposomal nanoparticles liposomal nanoparticles, wherein doxorubicin is present at concentration in the range from 50-500 µg/mL to obtain hydrogel containing gold-coated liposomal nanoparticles and doxorubicin.

The hydrogels disclosed herein may further comprise a pharmaceutically acceptable carrier or excipient. The carriers include, but are not limited to sterile aqueous media, solid diluents or fillers, excipients, and various non-toxic organic solvents.

The hydrogels as disclosed herein can be used as a medicament or as a component in a pharmaceutical composition. Pharmaceutical compositions include sprays, suppositories, pastes, ointments, jellies, lotions, injectable solutions, and parenteral solutions packaged in containers adapted for subdivision into individual doses.

Parenteral formulations include pharmaceutically acceptable aqueous or non-aqueous solutions, dispersion, emulsions, suspensions for the preparation thereof. Non-limiting examples of carriers include water, ethanol, polyols (such as propylene glycol, polyethylene glycol), vegetable oils, and injectable organic esters such as ethyl oleate. Fluidity can be maintained by the use of a coating such as lecithin, a surfactant, or maintaining appropriate particle size. Exemplary parenteral administration forms include solutions or suspensions of the compounds of the invention in sterile aqueous solutions, for example, aqueous propylene glycol or dextrose solutions. Such dosage forms can be suitably buffered, if desired.

In another embodiment, the invention provides a method for preventing or treating cancer by administration of a therapeutically effective amount of hydrogel as may be need on a case to case basis.

In certain embodiments, hydrogel may be administered in one or more dosage forms.

Those skilled in the art will be able to determine, according to known methods, the appropriate amount, dose or dosage of the hydrogel composition for administration to a subject taking into account factors such as age, weight, general health, the compositions administered, the route of administration, the nature and advancement of malignancy requiring treatment, and the presence of other medications.

The hydrogel may be administered together or independently of one another by any route known to a person skilled in the art, such as by oral, intravenous, topical, intraperitoneal or nasal route.

Preferable mode for administration of the hydrogels of the present invention is topical and intravenous administration.

In certain embodiments, the hydrogels are administered at a pre-determined daily dosage. This dosage regimen may be adjusted to provide the optimal therapeutic response. For example, the dose may be proportionally reduced or increased as indicated by the exigencies of the therapeutic situation.

The practice of the method of this invention may be accomplished through various administration or dosing regimens. The hydrogels of the present invention can be administered intermittently, concurrently or sequentially with other prescribed pharmaceutical compositions.

Repetition of the administration or dosing regimens may be conducted as necessary to achieve levels of treatment.

In one embodiment, the invention provides a hydrogel obtained by a method as described herein.

In another embodiment, the invention provides a method of treating cancer in a subject, comprising administering to the subject a therapeutically effective amount of a hydrogel of the present invention.

In another embodiment, the invention provides a method of treating cancer in a subject, comprising administering to the subject a therapeutically effective amount of the thermosensitive hydrogel of the present invention, wherein the hydrogel forms in situ nanoparticles and can be used for targeted therapeutics.

In another embodiment, the invention provides a method of treating cancer, wherein the thermosensitive hydrogel can target primary and metastasized secondary tumors.

In another embodiment, the invention provides a method of treating cancer, wherein the thermosensitive hydrogel can be used for treatment of primary and metastasized secondary tumors.

In another embodiment, the invention provides the use of hydrogel for targeted drug delivery to primary and metastasized secondary tumors and for bio-imaging.

EXAMPLES

The following examples particularly describe the manner in which the invention is to be performed. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Preparation of Liposomes and Gold-Coated Liposomes (LAu)

Liposomes and gold coated liposomes (LAu) were prepared for the invention. Briefly, Hydrogenated Soy Phosphatidyl Choline (HSPC) (obtained from Lipoid, Germany) was used for the preparation of liposome by thin film hydration method.

The dried lipid film was hydrated using Milli-Q and 2 mg/ml was kept as the working lipid concentration.

For the preparation of gold-coated liposomes (Lau), liposomes and $HAuCl_4$ were mixed in a volume ratio of 1:1 and ascorbic acid was used as reducing agent in 1:4 proportion. An immediate change in color of the solution indicates the reduction of $HAuCl_4$ on liposome template and successful preparation of gold-coated liposomes.

Example 2: Preparation of Poloxamer 407 (Pluronic-F127) Based Thermosensitive Hydrogel Three different types of gels were prepared: (1) thermosensitive PP hydrogel comprising Polyvinyl Alcohol (PVA) and poloxamer 407 (Pluronic-127); (2) thermosensitive PPA hydrogel comprising Polyvinyl Alcohol (PVA), poloxamer 407 (Pluronic 127) and Bovine Serum Albumin; and (3) thermosensitive PPA LAu hydrogel comprising PPA gel mixed with gold-coated liposomes (Lau) of Example 1.

For preparation of thermosensitive PP hydrogel, 2% of Polyvinyl Alcohol (PVA) solution obtained from Sigma Aldrich was added dropwise to 25% solution of poloxamer 407 (Pluronic 127) (w/v) obtained from Sigma Aldrich at 4° C. under constant stirring. The concentration of PVA may vary in the range between 2-6% v/v and the concentration of poloxamer 407 (Pluronic F-127) may vary in the range between 22-25% wt/v.

For preparation of thermosensitive gel PPA hydrogel, 2% solution of ice-cold Bovine Serum Albumin obtained from SRL was added dropwise to PP hydrogel under vigorous stirring for 6 hrs. The concentration of bovine serum albumin may vary in the range between 2-8% wt/v.

For the preparation of PPA LAu hydrogel, gold coated liposomal nanoparticles (LAu NPs) at a concentration of 2 mg/ml was added to PPA hydrogel at 4° C. under constant stirring for 10 minutes and mixture was injected through a 26-gauge syringe to evaluate the injectability of the hydrogel.

To evaluate the injectability of the prepared PPA hydrogel, the mixture was injected through a 26-gauge syringe. As shown in FIG. 1A. The prepared gel was thermosensitive and was injectable from a 26-gauge needle.

A hydrogel (PPA Dox LAu gel) containing gold coated liposomal nanoparticles (LAu NPs) and doxorubicin (dox) was prepared by mixing doxorubicin at a concentration of 500 μg/ml to the PPA LAu hydrogel by constant stirring.

Example 3: Thermoreversible/Irreversible (Gelation) of the Hydrogel

The thermoreversibility/irreversible nature of the hydrogel was evaluated by a test tube-inverting method. Briefly, the ice chilled PPA hydrogel solution was injected into a glass vial and incubated at physiological temperature (37° C.) for 5 minutes. Following the incubation, the glass vials was inclined to observe the fluidity of the hydrogel samples. The jellified hydrogel samples were incubated at 4° C. for 5 minutes to check the reversibility of the samples. It was found that the phase transition was reversible at 37° C.

To evaluate heat mediated thermal crosslinking of hydrogels the samples were then incubated for 5 minutes at elevated temperature (≈55° C.) and again at 4° C., then the glass vials was inclined to observe the fluidity/reversibility. As shown in FIG. 1A, the PPA hydrogel was cross-linked and did not exhibit any reversible behavior.

To evaluate NIR light mediated thermal crosslinking of LAu NPs entrapping hydrogels (PPA Lau hydrogel), the gel samples were subjected to laser (808 nm) irradiation for a duration of 10 min. The temperature of the sample was monitored by using thermal camera. After completion of laser exposure, the sample was incubated in 4° C. and again checked for gelling. It was observed that the NIR laser treated hydrogels were cross-linked and lost the reversibility (FIG. 1 B).

The above studies shows that the hydrogel when injected in the tumor can exhibit a phase transition from sol to gel at physiological temperature {(37° C.) reversible} and elevated temperature {(55° C.) irreversible} thus forming a depot.

The results indicate the suitability of the hydrogel to be used as a depot for sustained release of gold coated liposomal nanoparticle (LAu NPs) for PTT and micellar delivery of drug/dyes for therapeutics and bio imaging. The nanoparticle and the micelles releasing from the hydrogel can target and deliver drug to the newly metastasized foci thereby effectively suppressing the growth of secondary/metastasized tumors.

Example 4: Characterisation of PPA Hydrogel

The PPA hydrogel prepared in Example 2 were characterized.

Scanning Electron Microscopy (SEM) Analysis and Rheology

The morphological analysis of PPA hydrogel at physiological temperature (37° C.) and elevated temperature (55° C.) was evaluated using Scanning Electron Microscopy (SEM). The samples were dropped on a silica clean wafer. The samples were subjected to 37° C. and 55° C. for a duration of 10 min respectively. In another instance the samples containing LAu NPs were irradiated with NIR laser for 10 min.

Figure 2:
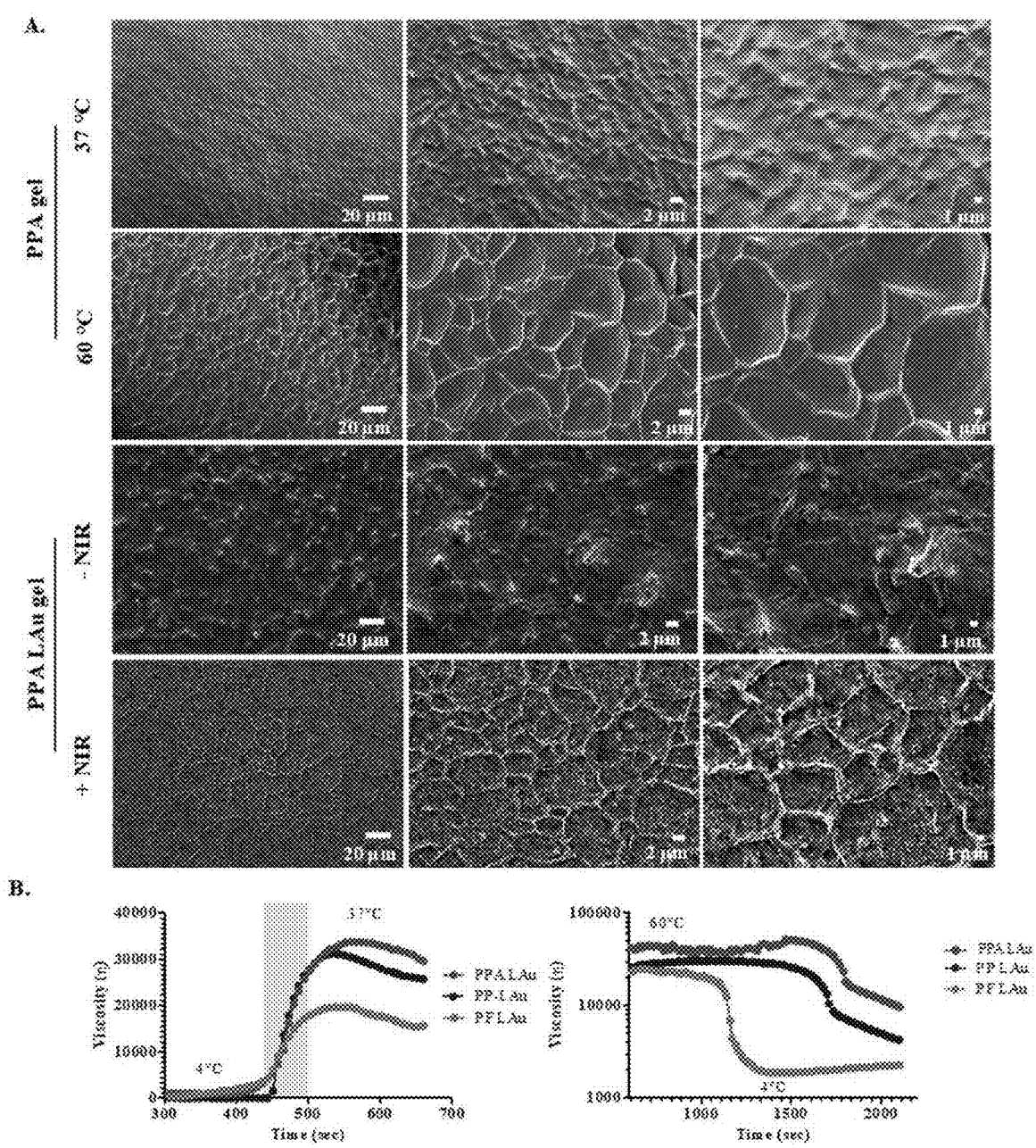
FIG. 2 depicts (A) SEM imaging of PPA gel at 37° C. and 60° C. and PPA LAu gel with/without NIR laser irradiation (B) Rheology of PF LAu NPs Gel, PP LAu NPs Gel and PPA LAu NPs gel.

Following the heat/NIR laser exposure, the samples were lyophilized, and sputter coated with gold for imaging. FIG. 2A indicates that the hydrogels gel samples placed at 37° C.

did not exhibit any characteristic morphological changes. However, both PPA gels and PPA LAu gel exposed to 55° C. and NIR laser exhibit a characteristic change in the gel morphology.

This change in morphological features of hydrogel exhibits NIR sensitivity of PPA LAu hydrogel. This also indicates the suitability of the hydrogels exposed to NIR to be used be used as a depot for sustained release of gold coated liposomal nanoparticle and/or sustained release of other drugs.

Rheological Characterization

The dynamic shear rheological properties of the hybrid hydrogel were evaluated under shear conditions at a frequency of 1 Hz using a DHR-1 temperature-controlled rheometer.

Briefly, a plate was lowered onto the sample with a nominal gap of ~1 mm to the facing specimen holder. Temperature-sweep dynamic shear test was conducted in a temperature range from 0 to 60° C. with a ramp rate of 5° C. min-1.

As shown in FIG. 2B, PPA LAu hydrogel exhibited a phase change that is similar to only poloxamer 407 gel, however when the temperature of the stage was elevated to 60° C. and then declined to 4° C. a significant change in the viscosity of the gels were noted. This change in the viscosity could be attribute to the irreversible crosslinking of PPA LAu hydrogels when exposed to elevated temperatures.

Example 5: In Vitro NIR Laser Triggered Sustained Drug Release

Doxorubicin (dox) was used as a model drug to study sustained drug release from the hydrogel. In vitro NIR laser triggered sustained release of doxorubicin (dox), a chemotherapeutic drug from PPA LAu hydrogel was evaluated by fluorescence spectroscopy.

Figure 3:
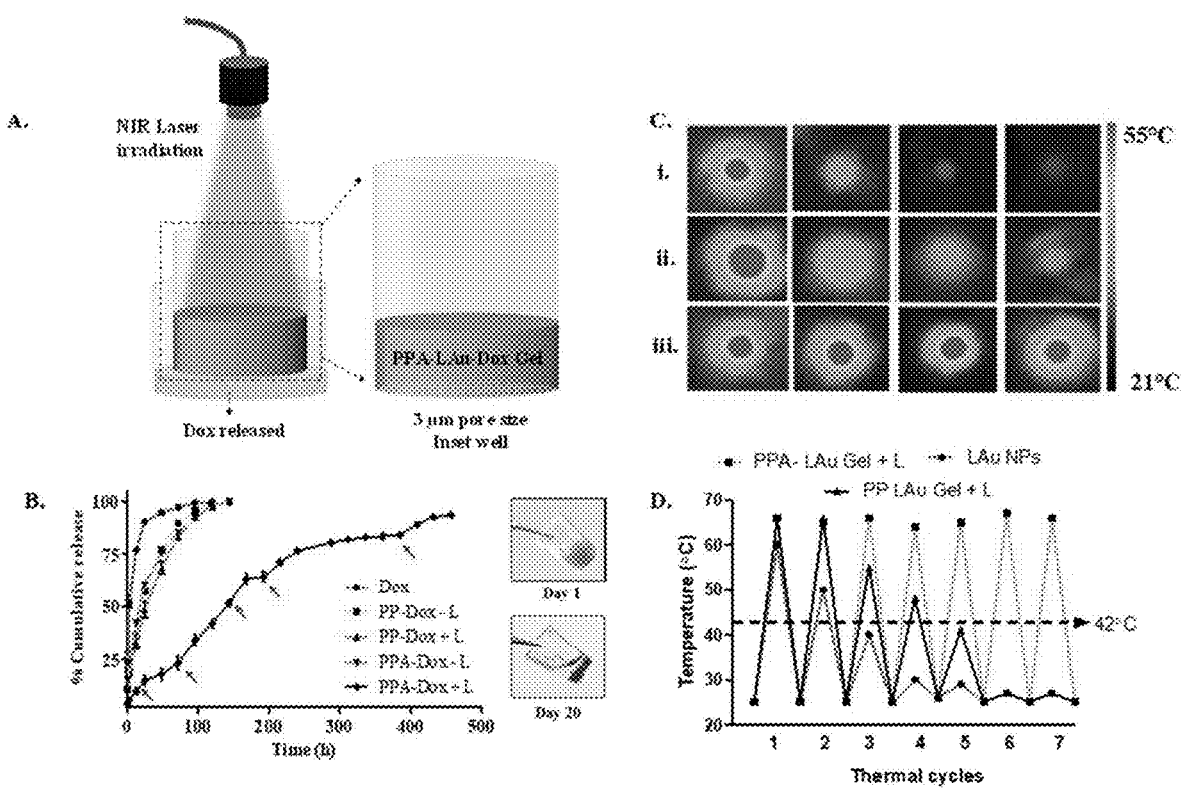
FIG. 3 depicts (A) Experimental setup for the evaluation of sustained photothermal effect and drug release, (B) NIR triggered sustained drug release of Dox from PPA LAu NPs Gel (Red arrows indicate NIR laser irradiation), (C) Thermal imaging of inset wells exhibiting sustained photothermal effect of PPA LAu NPs Gel, (D) Repeated trigger ability of PPA LAu NPs Gel.

Briefly, 300 μl of each hydrogel containing dox (500 μg/ml) was added to the inset (pore size=3 μm) of the trans-well plate and was subjected to laser irradiation for 10 minutes. These insets were then placed into the trans well containing 1 ml of PBS. A small aliquot of the PBS from the well was drawn to estimate the release of doxorubicin by using fluorescence spectroscopy. The sustained release of the chemotherapeutic drug was measured/recorded periodically for a duration of 20 days. The results are depicted in FIG. 3A and FIG. 3B.

The results depict the suitability of the hydrogel to be used as a delivery device for sustained release of hydrophobic drugs.

Example 6: In Vitro Photothermal Efficacy of PPA LAu Hydrogel

The sustained photothermal efficacy of PPA LAu hydrogel (and respective controls) were evaluated by using a NIR laser 808 nm (650 mW Shanghai lasers) in a trans-well plate as shown in the schematic of FIG. 4A.

Briefly, 300 μl of each hydrogel was added to the inset well (pore size=3 μm) of the trans-well plate and was subjected to 808 nm laser irradiation for 10 minutes. These insets were then placed to the trans well containing 1 ml of PBS.

The sustained photothermal efficacy of hydrogel was evaluated by recording the temperature at predetermined time intervals for a duration of 15 days, following NIR laser irradiation for 5 minutes the thermal images were captured using thermal camera (Flir, Chauvin Arnoux, CA, 1950 IR camera, USA).

A small aliquot of the PBS from the well was replaced with fresh PBS. It was observed that PPA LAu hydrogels were capable of maintaining sustained photothermal effect for about 15 days when compared with respective controls.

The results depict the suitability of the hydrogel to be used for photothermal therapy.

Example 7: Characterization of the LAu NPs Released from the Hydrogel

The gold-coated liposomal (Lau) nanoparticles which were released from the hydrogel were characterized by Transmission Electron Microscopy (TEM).

Transmission Electron Microscopy (TEM, JEM-2100F, JEOL Inc, USA) imaging was performed for studying the morphology of the particles released from the hydrogel. TEM was performed by drop casting the suspension on a copper grid.

As depicted in FIG. 4B and FIG. 4C, the nanoparticles released from the gel matrix after laser irradiation exhibited a drastic decline in size of the LAu NPs suggesting laser mediated degradation of nanoparticles.

The size reduction enables the nanoparticle to less than 10 nm can effectively lead to renal clearance from the biological system. Interestingly, it was observed that the hydrogel degrades into micelles like particles that are stable in physiological conditions.

The results indicate the suitability of the gold-coated nanoparticle loaded hydrogel to be used for metastasis targeting.

Example 8: Biocompatibility and the Laser Mediated Cell Cytotoxicity

The biocompatibility and the NIR laser mediated cell cytotoxicity of the hydrogels were evaluated in trans well plate of pore size 3 μm using methylthiazolyl diphenyl tetrazolium bromide (MTT) assays. Briefly, $1 \times 10^5$ cells of normal mouse fibroblast (NIH3T3) obtained from Center for Cellular and Molecular Biology (CCMB), Hyderabad were plated in the lower compartment of the trans well plate and incubated for 24 hr.

300 μl of each hydrogel was added to the inset (pore size=3 μm) of the trans-well plate and incubated at 37° C. for 5 minutes. The inset containing the cross-linked hydrogel was placed in the trans-well plate and incubated for 24 hrs. MTT assay was performed to evaluate the biocompatibility of the hydrogel.

The NIR laser mediated cell cytotoxicity of the PPA Dox, PPA LAu, PPA LAu Dox hydrogels were evaluated in melanoma cells (B16F10) obtained from National Centre for cell Science (NCCS), Pune, using MTT assay and also by live and dead assay.

Briefly, $1 \times 10^5$ cells were plated in the lower compartment of the trans well plate and incubated for 24 hr. 300 ul of each hydrogel was added to the inset (pore size=3 μm) of the trans-well plate and incubated at 37° C. for 5 minutes. The inset containing the cross-linked hydrogel was placed in the trans-well plate and irradiated with laser for 7 minutes.

Figure 5:
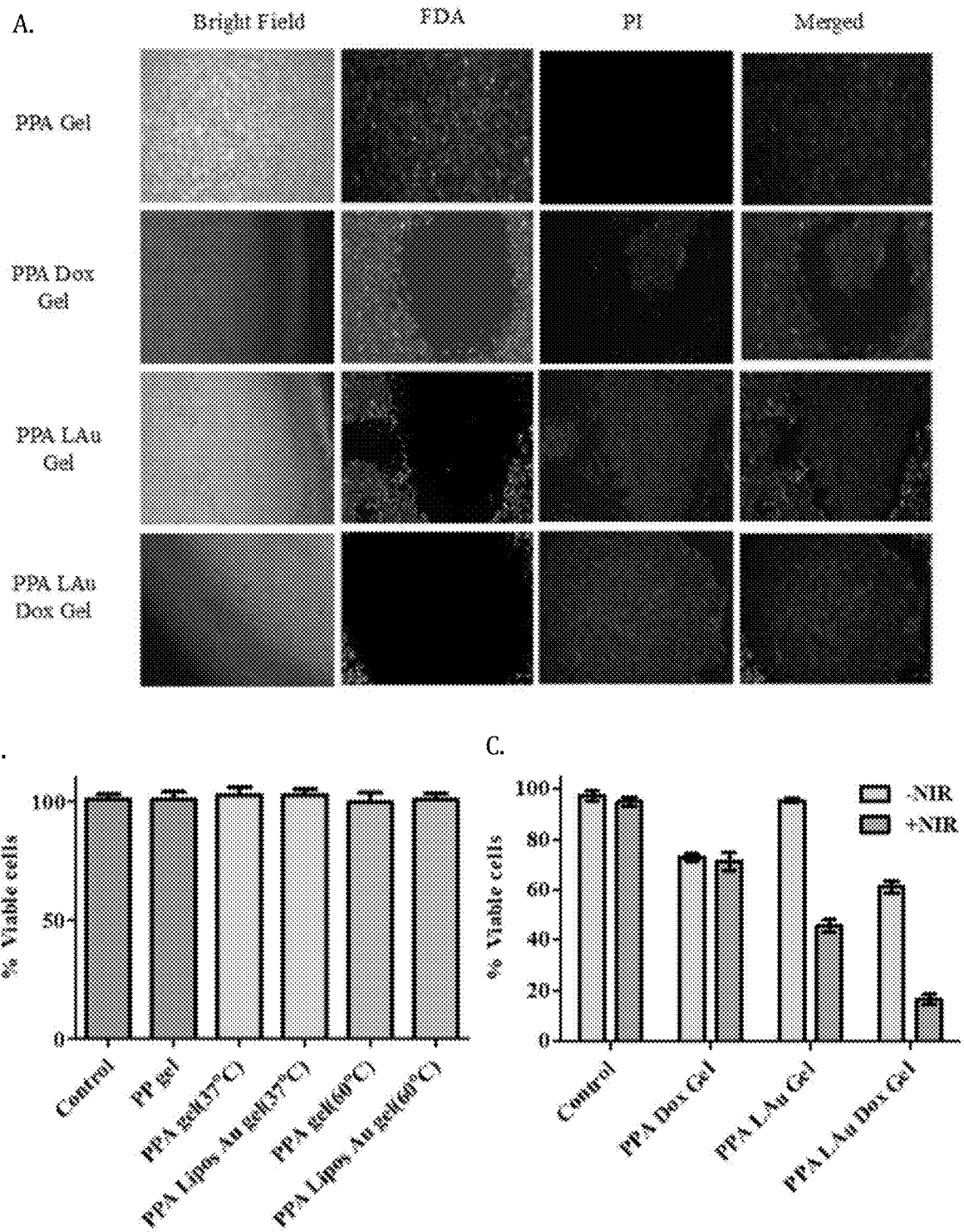
FIG. 5 depicts (A) Live/Dead analysis of PPA LAu NPs Gel on B16 cell line, (B) Biocompatibility of hydrogels in NIH 3T3 cell line (cross-linked at 37° C. and 60° C.), (C) MTT analysis of B16 cell line treated with PPA LAu NPs Dox Gel.

To evaluate the laser mediated cell cytotoxicity MTT assay was performed and Live dead assay was performed using FDA & PI to evaluate qualitatively. As depicted in FIG. 5A, FIG. 5B and FIG. 5C, the PPA LAu hydrogel exhibited excellent biocompatibility on normal fibroblast cells whereas selective toxicity when irradiated with NIR laser.

The NIR laser mediated cell cytotoxicity of the PPA Dox, PPA LAu, PPA LAu Dox hydrogels were evaluated in 3D cell culture model of melanoma cells (B16F10) using live and dead assay.

Briefly, 3D spheroids were cultured using hanging drop method. Briefly, $1\times10^4$ cells/drop were counted using hemocytometer, dropped onto the lid of a 60 mm cell culture plate and the lid was inverted to the PBS containing plate.

After day 4, the 3D aggregates were transferred to a non-adherent 96 well plate. After day 8 the 3D B16F10 spheroid was transferred to the trans well plate and laser mediated treatment was performed.

Live-dead assay was performed with FDA and PI staining for analyzing the cytotoxicity of the hydrogel qualitatively in the 3D B16F10 spheroid model.

After 4 hrs of laser irradiation, the spheroids are treated with FDA-propidium iodide staining (1 µM) and incubated for about 20 min at 37° C.

Figure 6:
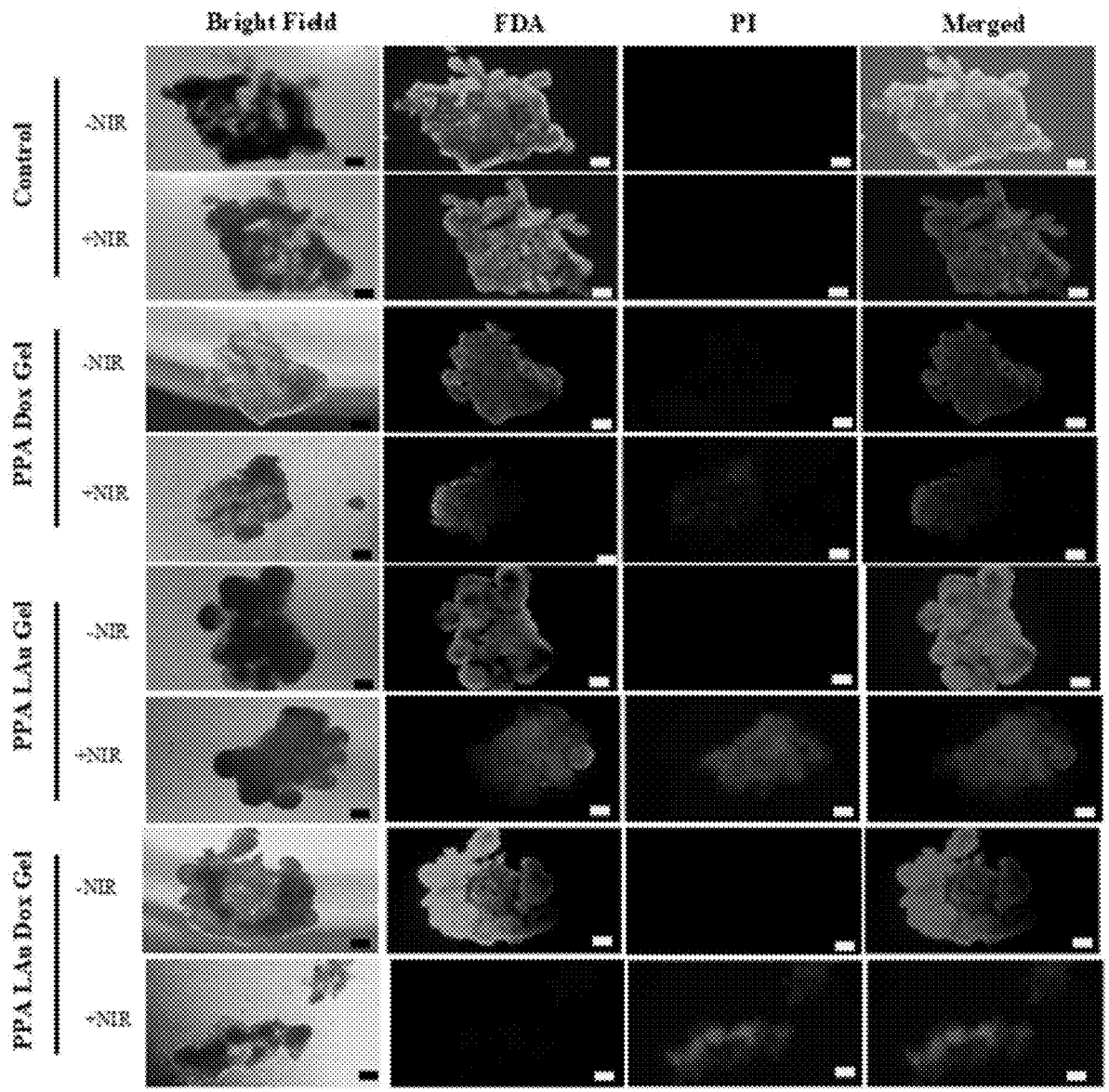
FIG. 6 depicts live/dead analysis of B16 cells spheroids treated with PPA LAu NPs Dox Gel.

The fluorescence images were captured by using 4× magnification using fluorescence microscope. As depicted in FIG. 6, the spheroids treated with PPA LAu Dox gel exhibited significant disruption of cancer cell spheroids when compared to respective controls.

The above studies demonstrate the biocompatibility, safety and efficacy of the hydrogels of the present invention.

Example 9: In Vivo Experiments

The in vivo experiments were conducted in compliance to CPCSEA guidelines and the study was approved by the Institutional Animal Ethics Committee of G. Pulla Reddy College of Pharmacy, Telangana, C57BL/6 female mice and Albino mice and BalB/C mice were procured from Hylasco Biotech, Hyderabad, India.

In Vivo Thermal Imaging and Sustained Photothermal Transduction Efficacy

The photothermal transduction efficacy for LAu NPs, PP LAu hydrogel, PPA LAu Hydrogel was evaluated in Albino mice (5-6 weeks old). The mice were weighed and randomly grouped into LAu NPs, PP LAu hydrogel, PPA LAu Hydrogel (3 groups).

300 µl of LAu NPs, PP LAu hydrogel, PPA LAu Hydrogel were injected subcutaneously and crosslinked by irradiating with NIR laser 808 nm (650 mW Shanghai lasers).

Figure 7:
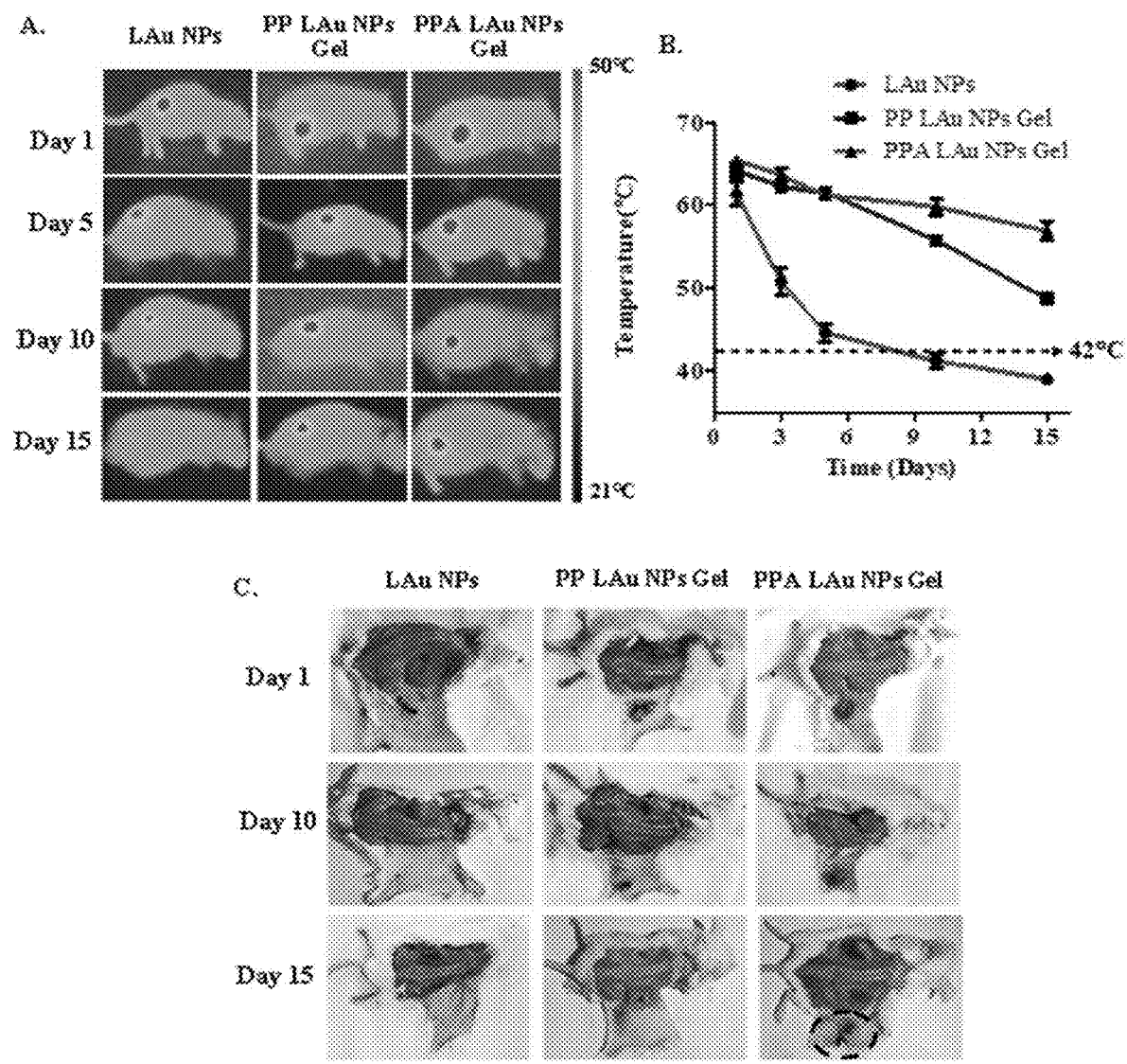
FIG. 7 depicts (A) In vivo thermal imaging of mice injected with hydrogels for sustained photothermal effect, (B) sustained photothermal effect of LAu NPs entrapped in PPA Gel, (C) Dissected animals exhibiting presence of gel depots till 15 days.

The sustained photothermal transduction efficacy was measured using thermal camera by irradiating the injected area with NIR laser in subsequent days (i.e. day 1, 3, 5, 7, 10, 15). As shown in FIG. 7A, FIG. 7B and FIG. 7C, the injected with PPA LAu gel exhibited a sustained photothermal effect till 15 days' post injection when compared with respective controls.

In Vivo Synergistic Antitumor Therapy

The melanoma tumor-bearing mouse was established by subcutaneously injecting $1\times10^6$ B16F10 cells into the dorsal flank region of the C57BL/6 female mice with an average weight of about 20 g.

After 10 days of tumor induction, when the tumor size reached to an average size of 500 mm³, the mice were randomly divided into five groups (n=5) Disease control, PPA gel+ laser, PPA Dox Gel +Laser, PPA LAu Gel+Laser and PPA Dox LAu Gel+ laser.

A peritumoral injection of 300 µl hydrogel was administered followed by the irradiation with NIR 808 nm laser for the cross linking of the hydrogel. The NIR laser irradiation was performed at tumor regions for 5 min on alternative days. A total of 3 treatments were given and tumor sizes were measured As depicted in FIG. 8A, the animals were monitored for the tumor growth and it was observed that PPA LAu Dox gel showed a significant decline in tumor growth following first treatment.

Figure 8:
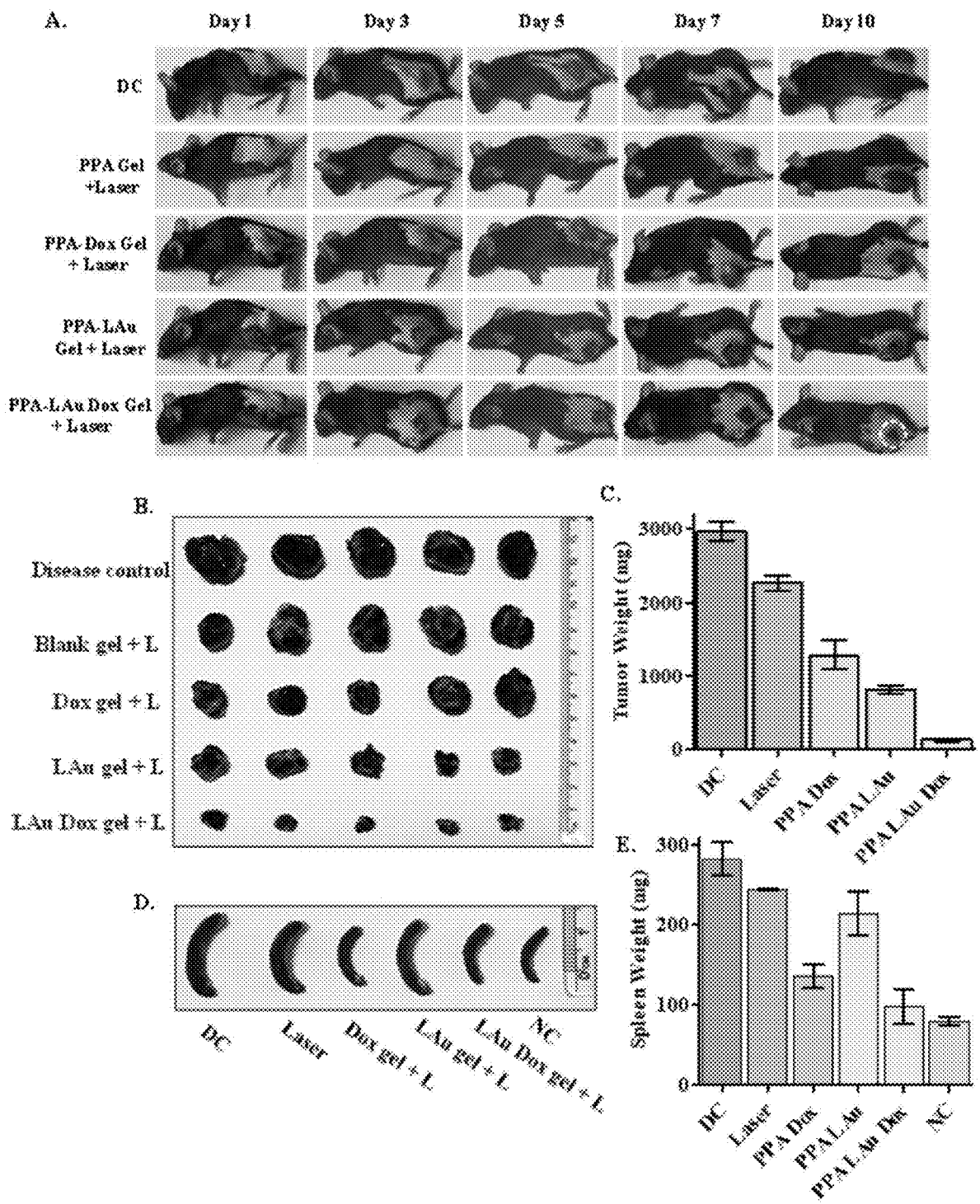
FIG. 8 depicts (A) In vivo tumor growth monitoring of B16 induced melanoma in C5BL6 mice, (B) Isolated tumors, (C) Tumor weight, (D) Isolated spleens and (E) Spleen weight of the treated animals.

By the end of the study the tumors were isolated and tumor weight was plotted (FIG. 8B and FIG. 8C). It was also observed that the PPA LAu Dox treated animals exhibited normal spleen size when compared to untreated animals (showing signs of splenomegaly) as shown in FIG. 8D and FIG. 8E.

The results indicate the safety and efficacy of the hydrogels.

Example 10: In Vivo Distal Tumor and Metastasis Targeting

Studies were conducted to evaluate the ability of PPA LAu hydrogel to target distal tumors and lung metastasis was evaluated by using a small animal NIR fluorescence imaging system (IVIVS Perkin Elmer).

Figure 9:
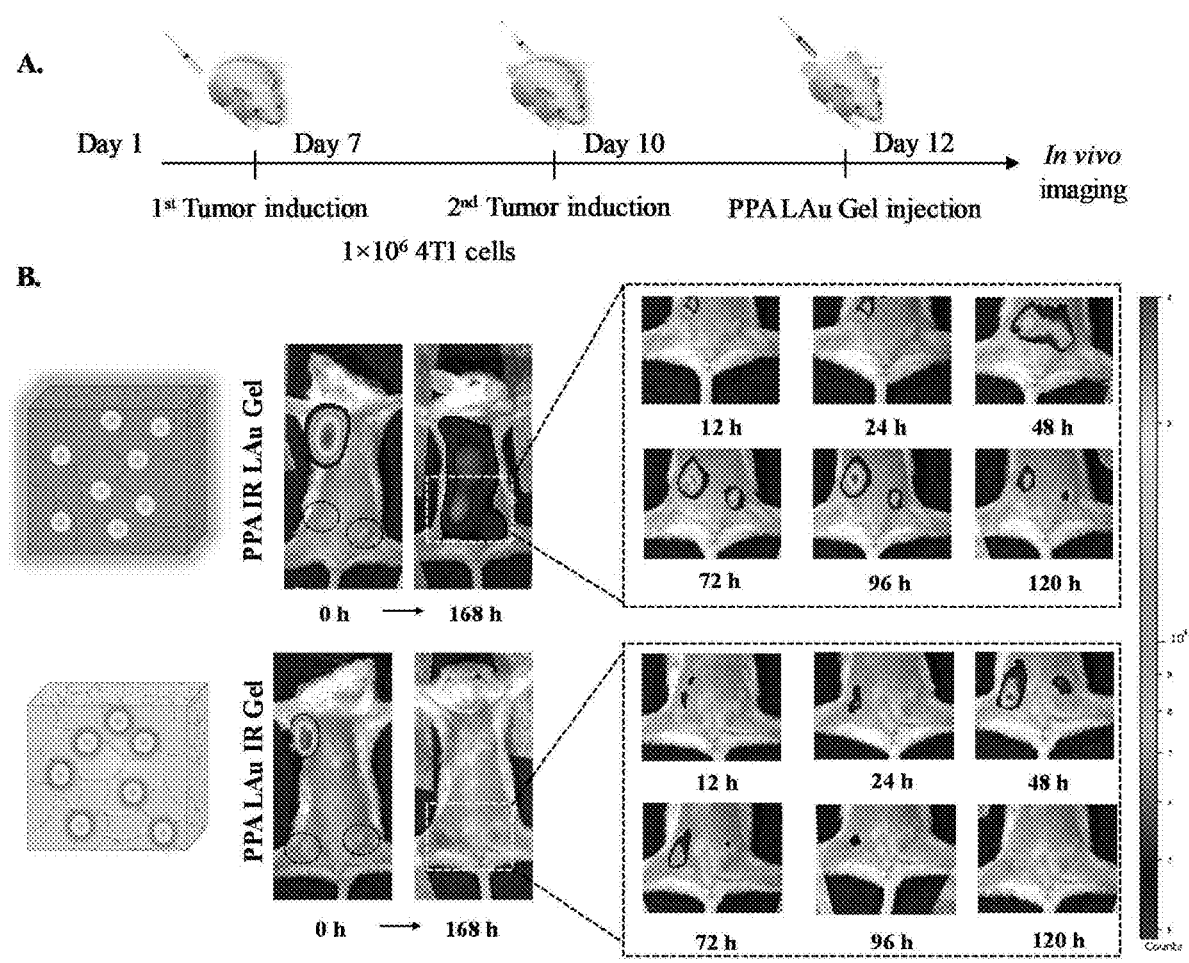
FIG. 9 depicts tumor targeting by PPA LAu NPs gel (IR 780 dye was used for imaging).

An orthotropic 4T1 tumor was established in BalB/C mice by injecting $1\times10^6$ 4T1 cells in mammary fat pads (both sides). One side of the tumors were injected by a delay of 1 week following the induction of first tumor. A 200 µl of PPA LAu gel (entrapping IR 780 dye) was injected in the right upper flank of the animal. Following the injection animals were monitored for the distribution of NIR dye by imaging system. As shown in FIG. 9A and FIG. 9B the animals treated with PPA LAu gel entrapping IR 780 dye exhibited targeting of distal tumors of varying growth rate.

Figure 10:
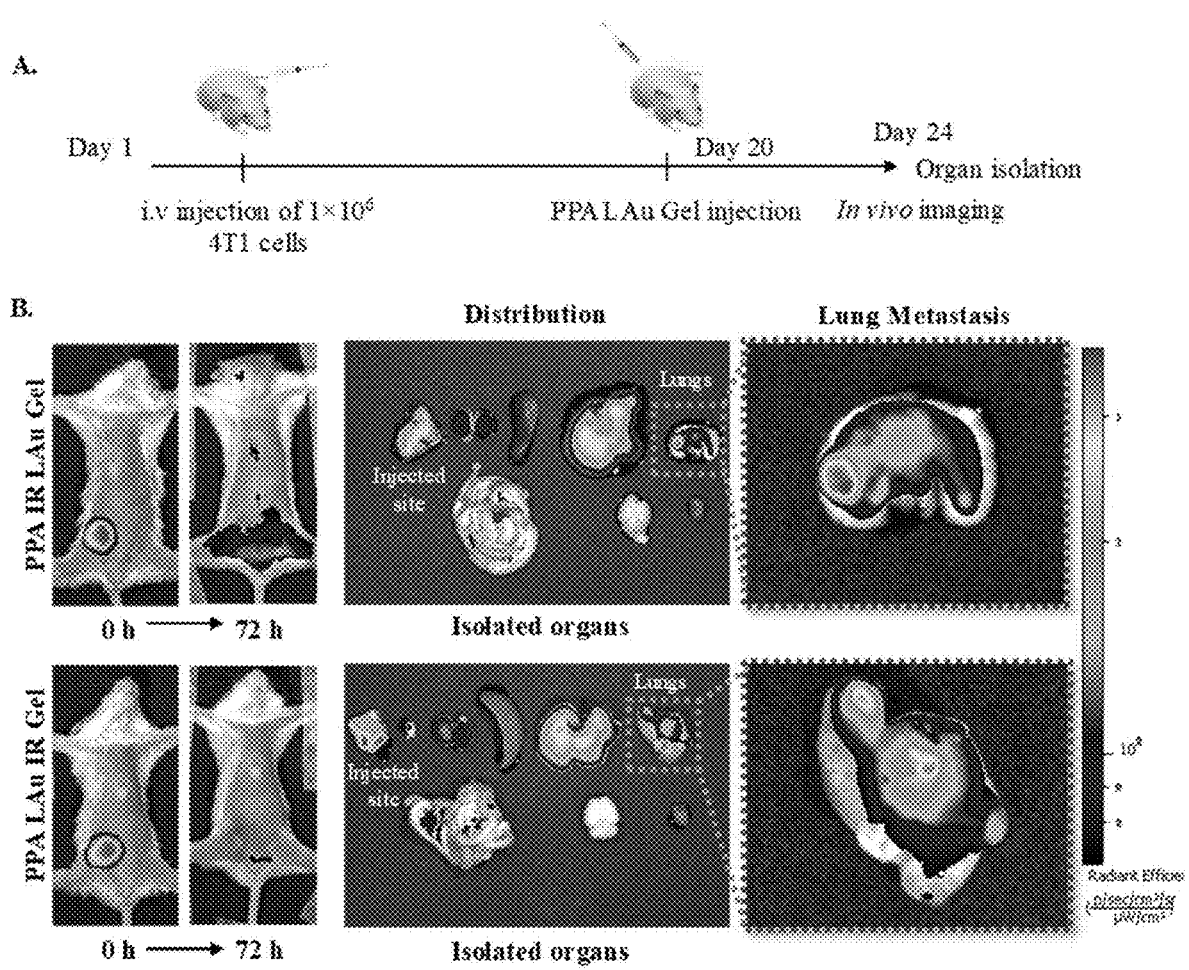
FIG. 10 depicts lung metastasis targeting by PPA LAu NPs gel (IR 780 dye was used for imaging).

The lung metastasis model was established by injecting $1\times10^6$ 4T1 cells by i.v. following the injection animals were injected with PPA LAu hydrogel entrapping IR 780 dye on $20^{th}$ day. Later animals were monitored for the localization of NIR dye by using small animal imaging system. As shown in FIG. 10A and FIG. 10B the animals treated with PPA LAu gel entrapping IR 780 dye exhibited as sustained targeting of lung tumors for a period of 168 h (shown in isolated organs) this suggests the ability if PPA LAu hydrogel system to target metastasized lung tumors.

Example 11: pH Dependent Release of Doxorubicin from PPA Hydrogel

It was found that PPA LAu hydrogel comprising doxorubicin forms in situ nanoparticles. The pH-dependent release of doxorubicin was evaluated at three different pH: (i) physiological pH of 7.4 (ii) pH of the tumor microenvironment at 6.4 and (iii) acetate buffer at 5.8.

Briefly, doxorubicin-loaded PPA LAu Nanoparticles were suspended in 1 mL of buffer with 3 different pH and were incubated at 37° C. at 50 rpm. The buffer from the 2 mL tube was drawn at specific time intervals to estimate dox release by using fluorescence spectroscopy and was replaced with fresh buffer. The sustained release of the chemotherapeutic drug was recorded periodically and the experiment was done in triplicates.

Figure 11:
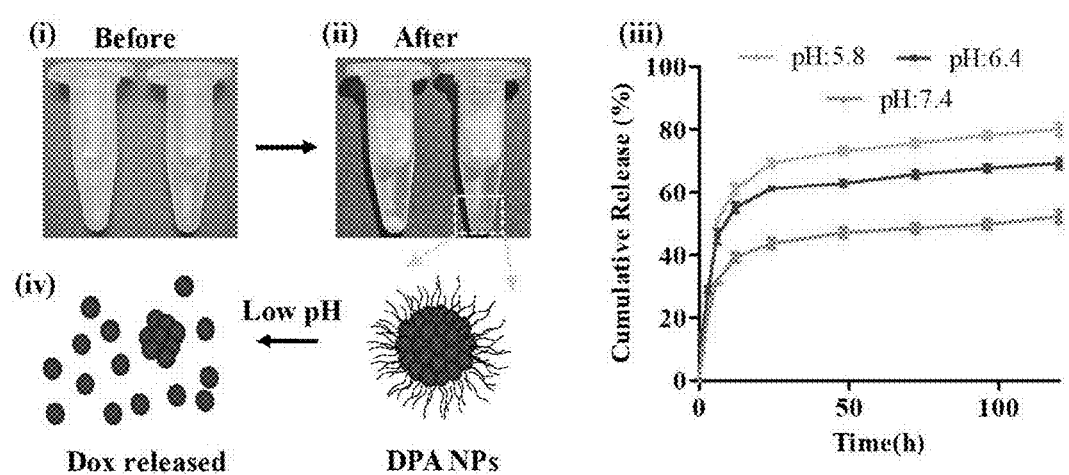
FIG. 11 depicts: (i) & (ii) Isolated PPA nanoparticles and DPA nanoparticles (doxorubicin entrapping PPA NPs) before and after centrifugation exhibiting pellet formation. (iii) & (iv) Dox release kinetics from DPA NPs when suspended at varying pH 5.8, 6.4 and 7.4, and schematic representing the drug release.

The doxorubicin-loaded PPA LAu nanoparticles showed a pH responsive release with about ~80%, ~70% and ~50% of Dox being released within 120 h at pH 5.8, 6.4 and 7.4 respectively. The results are provided in FIG. 11.

These finding confirmed that the in-situ formed PPA LAu nanoparticles can not only entrap the drug but also exhibit a pH responsive drug release. The pH responsiveness of PPA LAu nanoparticles could holds significant importance in inhibiting aggressive metastatic tumors as they are known to have acidic microenvironment. Delivering the chemotherapeutic agents to metastasized tumors combined with pH based drug release can be an effectively therapeutic strategy for inhibiting metastasis.

Example 12: Therapeutic Efficacy of PPA Dox LAu Gel on Spontaneous Metastasis Model The spontaneous melanoma metastatic lung nodule bearing mouse was established by intravenous injection of $2\times10^5$ B16F10 cells into the tail region of the C57BL/6 female mice with an average weight of ~20 g.

On the 10th day of tumor injection, the mice were randomly divided into four groups (n=5) Disease control, Free Dox, PPA LAu Dox Gel and PPA Dox LAu gel.

300 µL of the hydrogel was administered subcutaneously on every 4th day, and five doses of treatment were given. After 35 days, the mice were sacrificed for the analysis of the spontaneous melanoma metastatic lung nodules. The weight of the lungs was measured and compared with the normal lungs. Ex vivo quantification of melanin from isolated lungs of each group was done with a slight modification of the previous literature. 100 mg of the lung samples from each group was dissolved in 1M NaOH containing 10% DMSO. The samples were heated at 80° C. for 1 h and centrifuged at 3000 g for 10 min. The UV-Visible absorbance of the supernatant was measured at 410 nm.

Figure 12:
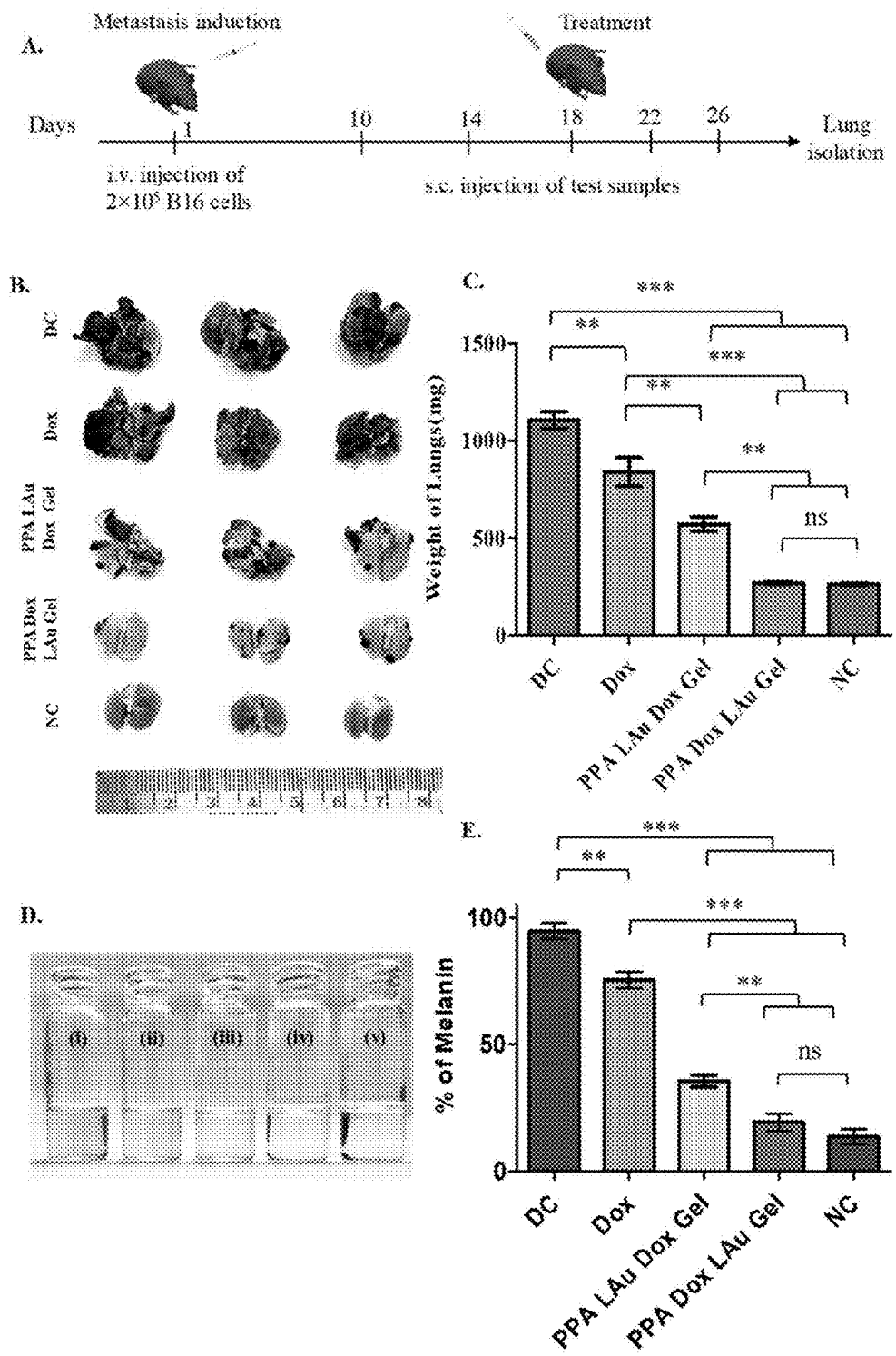
FIG. 12 depicts (A) Schematic representation of spontaneous metastasis induction and treatment by PPA Dox Lau gel, (B) Isolated lungs representing lung nodules (C) weight of isolated lungs of animals treated with disease control, Dox, PPA Lau Dox gel, PPA Dox Lau gel and normal control. (D) melanin extracted from isolated lungs from the treated animals. (E) Quantification of melanin extracted from animals treated by with disease control, Dox, PPA Lau Dox gel, PPA Dox Lau gel and normal control.

As can be seen from FIG. 12, by the end of the study period there was a significant suppression of metastatic lung nodules formed in PPA Dox LAu gel treated groups when compared to Dox treated and disease control groups.

The substantial inhibition of lung nodules in PPA Dox LAu gel was attribute to the release of DPA NPs from the injected site, which got accumulated within the tumor nodules and released the drug. This was also confirmed by the lung weight were the untreated mice showed ~5 fold increase in the weight of lungs compared to normal control. The melanin was also quantified from the isolated lungs, and it was observed that the PPA Dox LAu gel treated group showed minimal melanin when compared to disease control and dox treated groups suggesting the inhibition of metastasis and possible radiation sensitization.

We claim:

1. A thermosensitive hydrogel comprising polyvinyl alcohol, poloxamer 407 and bovine serum albumin, and a pharmaceutically acceptable carrier that comprises sterile aqueous media, solid diluents, fillers, excipients, and plural non-toxic organic solvents, wherein the polyvinyl alcohol is a water-soluble polymer and the poloxamer is a tri-block polymer that includes a central hydrophobic block of polypropylene glycol (PPG) flanked by two hydrophilic blocks of polyethylene glycol (PEG).

2. The hydrogel as claimed in claim 1, wherein the hydrogel contains one or more additional components selected from a group consisting of photothermal agents, photosensitizers, vaccines, proteins, drugs and dyes.

3. The hydrogel as claimed in claim 1, wherein the concentration of polyvinyl alcohol in the hydrogel is in a range from 2-5% v/v.

4. The hydrogel as claimed in claim 1, wherein the concentration of poloxamer 407 in the hydrogel is in a range from 22-25% wt/v.

5. The hydrogel as claimed in claim 1, wherein the concentration of bovine serum albumin in the hydrogel is in a range from 2-8%.

6. The hydrogel as claimed in claim 2, wherein the photothermal agent is gold-coated liposomal nanoparticles.

7. The hydrogel as claimed in claim 2, wherein the drug is a hydrophobic drug.

8. The hydrogel as claimed in claim 7, wherein the drug is doxorubicin.

9. A method for preparing the thermosensitive hydrogel as claimed in claim 1, comprising:
   a. adding polyvinyl alcohol to a solution of poloxamer 407 under constant stirring at a temperature in the range from 2-6° C., wherein the concentration of polyvinyl alcohol is in a range of 2-5% v/v and the concentration of poloxamer 407 is in a range of 22-25% wt/v; and
   b. adding 2-8% solution of ice-cold bovine serum albumin to the reaction mixture obtained in step (a) under vigorous stirring for about 6 hrs to obtain a thermosensitive hydrogel.

10. The method as claimed in claim 9, wherein the thermosensitive hydrogel obtained in step (b) is enriched with one or more additional component selected from a group comprising photothermal agents, photosensitizers, vaccines, proteins, drugs and dyes.

11. A method for preparing the thermosensitive hydrogel as claimed in claim 1 containing gold-coated liposomal nanoparticles and doxorubicin, comprising:
   a. adding polyvinyl alcohol to a solution of poloxamer 407 under constant stirring at a temperature in the range from 2-6° C., wherein the concentration of polyvinyl alcohol is in a range of 2-5% v/v and the concentration of poloxamer 407 is in a range of 22-25% wt/v;
   b. adding 2-8% solution of ice cold bovine serum albumin to the reaction mixture obtained in step (a) under vigorous stirring for about 6 hrs to obtain a thermosensitive hydrogel;
   c. adding gold coated liposomal nanoparticles to the hydrogel obtained in step (b) at a temperature about 4° C. under constant stirring for 10 minutes, wherein the concentration of gold-coated nanoparticles ranges from 1-3 mg/mL to obtain hydrogel containing gold-coated liposomal nanoparticles; and
   d. adding doxorubicin to the gold-coated liposomal nanoparticles liposomal nanoparticles, wherein doxorubicin is present at concentration in the range from 50-500 µg/mL to obtain hydrogel containing gold-coated liposomal nanoparticles and doxorubicin.

12. A pharmaceutical composition comprising the hydrogel recited in claim 1.

13. A hydrogel obtained by the method as claimed in claim 9.

14. A hydrogel obtained by the method as claimed in claim 11.

15. The thermosensitive hydrogel as claimed in claim 1 comprising polyvinyl alcohol and poloxamer 407, wherein the concentration of polyvinyl alcohol in the hydrogel is in a range from 2-6% v/v, the concentration of poloxamer 407 in the hydrogel is in a range from 22-25% wt/v.

16. The thermosensitive hydrogel as claimed in claim 1 comprising polyvinyl alcohol, poloxamer 407 and bovine serum albumin, wherein the concentration of polyvinyl alcohol in the hydrogel is in a range from 2-6% v/v, the concentration of poloxamer 407 in the hydrogel is in a range from 22-25% wt/v and the concentration of bovine serum albumin in the hydrogel is in a range from 2-8% wt/v.

17. A thermosensitive hydrogel as claimed in claim 1 comprising polyvinyl alcohol, poloxamer 407, bovine serum albumin, gold-coated liposomal nanoparticles and doxorubicin, wherein the concentration of polyvinyl alcohol in the hydrogel is in a range from 2-5% v/v, the concentration of poloxamer 407 in the hydrogel is in a range from 22-25% wt/v, the concentration of bovine serum albumin in the hydrogel is in a range from 2-8% wt/v, the concentration of liposomal nanoparticles in the hydrogel is in a range from 1-3 mg/ml and the concentration of doxorubicin in the hydrogel is in a range from 50-500 µg/ml.

18. A method of treating cancer in a subject, comprising administering to the subject a therapeutically effective amount of the hydrogel as claimed in claim 1.

19. A method of treating cancer in a subject, comprising administering to the subject a therapeutically effective amount of the hydrogel as claimed in claim 1, wherein the hydrogel forms in situ nanoparticles and can be used for targeted therapeutics.

20. A method of treating cancer as claimed in claim 18, wherein the thermosensitive hydrogel can target and treat primary and metastasized secondary tumors.

* * * * *